US010260929B2

(12) United States Patent
Kassubek et al.

(10) Patent No.: US 10,260,929 B2
(45) Date of Patent: Apr. 16, 2019

(54) SYSTEM AND METHOD FOR MEASURING A SIGNAL PROPAGATION SPEED IN A LIQUID OR GASEOUS MEDIUM

(71) Applicant: ABB Schweiz AG, Zürich (CH)

(72) Inventors: Frank Kassubek, Rheinfelden (DE); Miklos Lenner, Baden-Dättwil (CH); Tobias Kaufmann, Zürich (CH); Detlef Pape, Nussbaumen (CH)

(73) Assignee: ABB Schweiz AG, Baden (CH)

( * ) Notice: Subject to any disclaimer, the term of this patent is extended or adjusted under 35 U.S.C. 154(b) by 357 days.

(21) Appl. No.: 15/202,177

(22) Filed: Jul. 5, 2016

(65) Prior Publication Data

US 2017/0010143 A1 Jan. 12, 2017

(30) Foreign Application Priority Data

Jul. 6, 2015 (EP) ...................................... 15002011
Nov. 25, 2015 (EP) ...................................... 15196352

(51) Int. Cl.
*G01H 5/00* (2006.01)
*G01S 7/40* (2006.01)
(Continued)

(52) U.S. Cl.
CPC ........ *G01F 23/284* (2013.01); *G01F 23/2962* (2013.01); *G01F 23/2968* (2013.01);
(Continued)

(58) Field of Classification Search
CPC ............... G01F 23/284; G01F 23/2845; G01F 23/2961; G01F 23/2962; G01F 25/0061; G01H 5/00; G01N 29/024
See application file for complete search history.

(56) References Cited

U.S. PATENT DOCUMENTS 5,616,856 A * 4/1997 Castel ................. G01F 23/2962
73/61.44
5,777,230 A * 7/1998 Vandervalk ........... B06B 1/0662
73/1.82
(Continued)

FOREIGN PATENT DOCUMENTS

JP 2006322825 A 11/2006

*Primary Examiner* — Peter M Bythrow
(74) *Attorney, Agent, or Firm* — Taft Stettinius & Hollister LLP

(57) ABSTRACT

A system and a method for measuring a signal propagation speed in a liquid contained in a vessel or in a gaseous medium contained in the same vessel above the surface of the liquid are proposed. A transmitter transmits a first signal in a first direction which is at an acute or right angle to a first reflective surface, wherein the first reflective surface reflects the first signal so that it travels in a second direction is received by a first acoustic or electromagnetic receiver. The transmitter transmits a second signal in a predetermined third direction which is at an acute angle to the first direction, where the first or a second reflective surface reflects the second signal so that it travels in a predetermined and angular fourth direction with respect to the first or second reflective surface and is received by the first or a second acoustic or electromagnetic receiver. The speed of sound is then determined under the assumption that both the first and the second signals travel at the same average speed.

20 Claims, 5 Drawing Sheets

Figure 2:
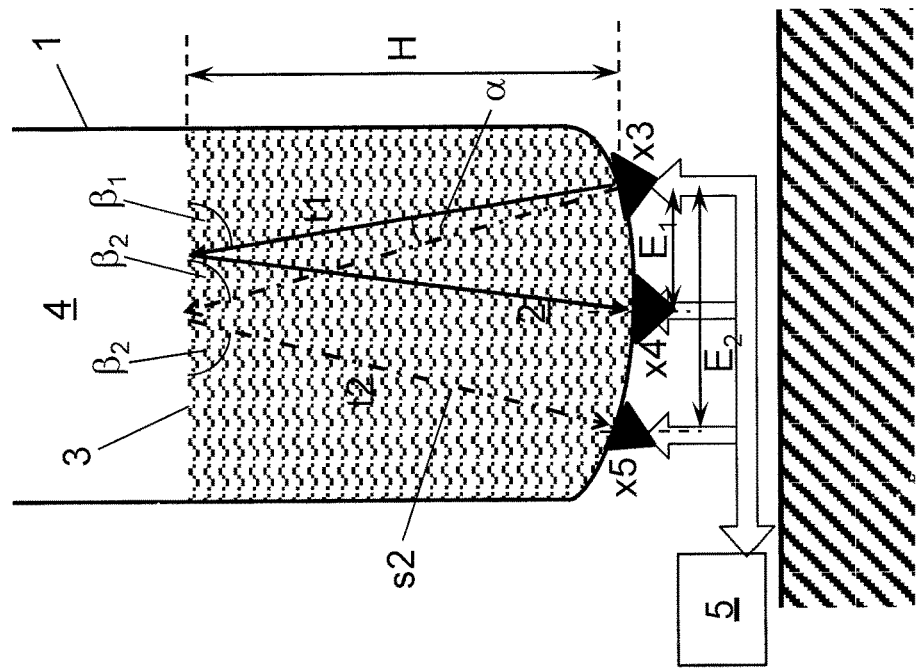

(51) Int. Cl.
- *G01S 7/52* (2006.01)
- *G01F 25/00* (2006.01)
- *G01N 29/22* (2006.01)
- *G01S 13/00* (2006.01)
- *G01S 13/10* (2006.01)
- *G01S 13/46* (2006.01)
- *G01S 13/87* (2006.01)
- *G01S 13/88* (2006.01)
- *G01S 15/00* (2006.01)
- *G01S 15/10* (2006.01)
- *G01S 15/87* (2006.01)
- *G01S 15/88* (2006.01)
- *G01S 7/539* (2006.01)
- *G01F 23/284* (2006.01)
- *G01F 23/296* (2006.01)
- *G01N 29/024* (2006.01)

(52) U.S. Cl.
CPC ........ G01F 25/0061 (2013.01); G01H 5/00 (2013.01); G01N 29/024 (2013.01); G01N 29/222 (2013.01); G01S 7/40 (2013.01); G01S 7/52006 (2013.01); G01S 7/539 (2013.01); G01S 13/878 (2013.01); G01S 13/88 (2013.01); G01S 15/878 (2013.01); G01S 15/88 (2013.01); *G01N 2291/011* (2013.01); *G01N 2291/02836* (2013.01); *G01S 13/003* (2013.01); *G01S 13/10* (2013.01); *G01S 15/003* (2013.01); *G01S 15/10* (2013.01); *G01S 2013/462* (2013.01)

(56) References Cited

U.S. PATENT DOCUMENTS

| | | | | |
|---|---|---|---|---|
| 6,053,041 A * | 4/2000 | Sinha | | G01F 23/28 340/621 |
| 6,925,870 B2 | 8/2005 | Pappas et al. | | |
| 7,304,601 B1 * | 12/2007 | Edvardsson | | G01F 23/284 342/118 |
| 8,661,904 B2 * | 3/2014 | Schmitt | | G01B 17/025 73/290 V |
| 2003/0117150 A1 * | 6/2003 | Noik | | B01D 19/0063 324/639 |
| 2004/0119635 A1 * | 6/2004 | Edvardsson | | G01F 23/284 342/124 |
| 2004/0229376 A1 * | 11/2004 | Beauducel | | G01F 23/2845 436/164 |
| 2005/0179584 A1 * | 8/2005 | Ohlsson | | G01F 23/284 342/124 |
| 2006/0201246 A1 * | 9/2006 | Rolfes | | G01B 15/04 73/290 V |
| 2007/0028684 A1 * | 2/2007 | Benz | | G01F 23/284 73/314 |
| 2007/0194799 A1 * | 8/2007 | Carobbio | | G01F 23/284 324/644 |
| 2009/0066966 A1 * | 3/2009 | Baath | | G01F 23/284 356/503 |
| 2009/0128395 A1 * | 5/2009 | Baath | | G01F 23/284 342/124 |
| 2009/0158839 A1 * | 6/2009 | Spanke | | G01F 23/284 73/290 V |
| 2009/0315758 A1 * | 12/2009 | Jirskog | | G01F 23/284 342/124 |
| 2010/0019952 A1 * | 1/2010 | Poussin | | B01J 8/0015 342/124 |
| 2010/0090883 A1 * | 4/2010 | Chen | | G01F 23/284 342/124 |
| 2010/0101317 A1 * | 4/2010 | Ashrafzadeh | | G01F 23/0061 73/149 |
| 2010/0162811 A1 * | 7/2010 | Malinovskiy | | G01F 23/284 73/290 V |
| 2010/0213922 A1 * | 8/2010 | Sadri | | B22D 2/003 324/72 |
| 2010/0313654 A1 * | 12/2010 | Malinovskiy | | G01F 23/0061 73/304 C |
| 2011/0166805 A1 * | 7/2011 | Hammer | | G01F 23/284 702/55 |
| 2011/0272866 A1 * | 11/2011 | Shameli | | F27B 3/085 266/78 |
| 2013/0132005 A1 * | 5/2013 | Welle | | G01F 23/284 702/55 |
| 2014/0085132 A1 * | 3/2014 | Jirskog | | G01F 23/284 342/124 |
| 2014/0136127 A1 * | 5/2014 | Sanchez Galicia | | G01F 23/284 702/55 |
| 2014/0208845 A1 * | 7/2014 | Zlotnick | | G01F 22/00 73/290 V |
| 2014/0340259 A1 * | 11/2014 | Fehrenbach | | G01S 13/02 342/359 |
| 2015/0007653 A1 * | 1/2015 | Fehrenbach | | G01P 5/242 73/198 |
| 2015/0007654 A1 * | 1/2015 | Fehrenbach | | G01P 5/00 73/198 |
| 2015/0007655 A1 * | 1/2015 | Skowaisa | | G01S 13/34 73/198 |
| 2015/0048963 A1 * | 2/2015 | Dieterle | | G01F 23/284 342/5 |
| 2015/0061919 A1 * | 3/2015 | Bilgic | | G01S 7/02 342/124 |
| 2015/0226594 A1 * | 8/2015 | Frovik | | G01F 23/284 342/124 |
| 2015/0253177 A1 * | 9/2015 | Blodt | | G01F 23/284 324/644 |

* cited by examiner

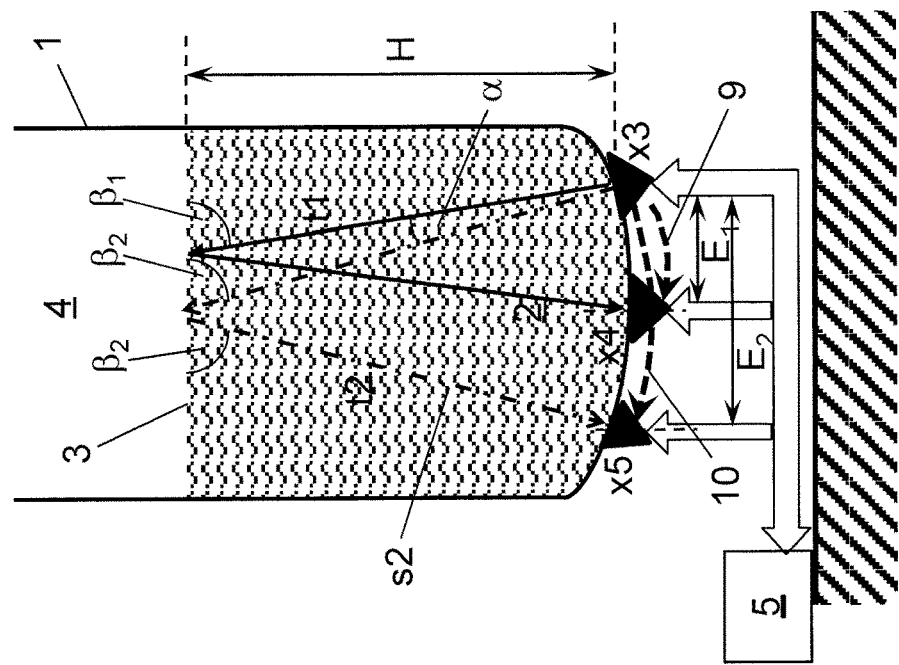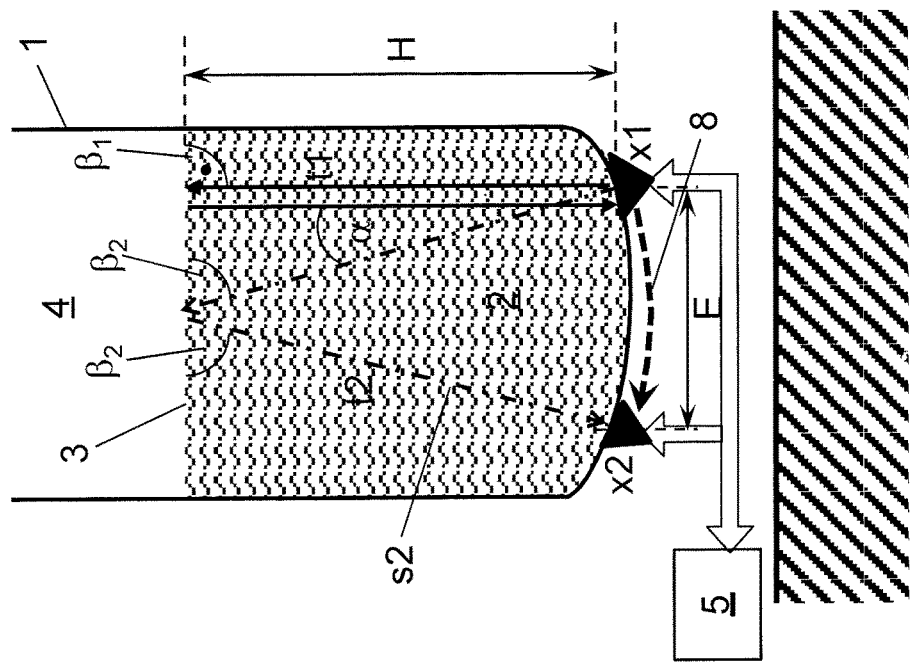

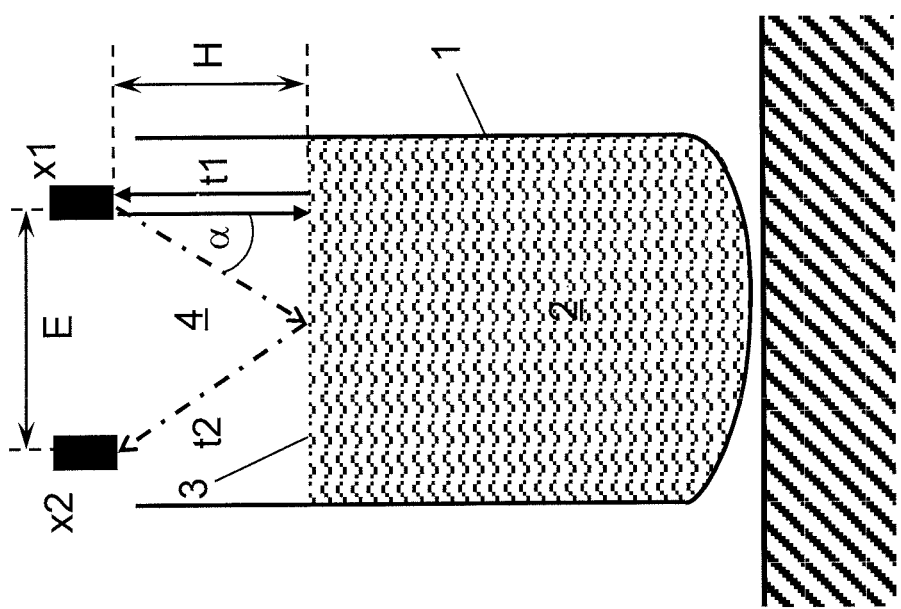

SYSTEM AND METHOD FOR MEASURING A SIGNAL PROPAGATION SPEED IN A LIQUID OR GASEOUS MEDIUM

The invention relates to a system and a method for measuring a signal propagation speed in a liquid contained in a vessel, or in a gaseous medium contained in the same vessel above the surface of the liquid.

In order to determine the filling level of a vessel it is important to know the signal propagation speed in a liquid or in a gaseous medium, i.e. to know the propagation speed of an acoustic or electromagnetic wave that travels through the medium.

For continuously determining the filling level, continuous level sensors are used, opposed to point level sensors which only detect whether a predefined level is exceeded by a liquid surface or not. Nowadays, continuous level measurement methods mainly use an intrusive technique i.e. an opening in the wall of the vessel is needed to introduce the level sensor into the vessel. The intrusive techniques may be based on acoustic or electromagnetic signals that are sent towards the liquid surface from which they are reflected back.

However, in certain industries, such as in the food or pharmaceutical industry, it is undesirable to bring a foreign object into close proximity of or even contact with the liquid, in order to avoid contamination. In even other areas, such as in the chemical or in the oil and gas industry, intrusive level measurement may not be indicated due to the liquids being explosive, easily inflammable or corrosive or being subject to extreme temperatures. For these conditions, non-intrusive continuous level measurement techniques are used which are based on measuring the filling level of a closed vessel.

The majority of continuous level measurement methods are based on the time of flight measurement of an acoustic or electromagnetic pulse. In these devices, a pulse is sent for example from the bottom of a tank or vessel through the liquid towards the interface between the liquid and a gas that fills the space above the liquid. Alternatively, the pulse is sent in the opposite direction from the inner top of the vessel through the gas to the interface. This interface may also be called liquid surface or level interface. From the level interface, the pulse is reflected back, and received again at a certain location. The propagation distance L and thus the height of the level interface can then be calculated by dividing the propagation time t of the pulse by the propagation velocity c, under the assumption that the propagation velocity c is known and is constant along the entire propagation path.

In JP2006322825A, a non-intrusive liquid level measuring method is described which applies above described level measuring technique, i.e. which measures the time of flight of an ultrasonic pulse transmitted from the outside of the bottom of the tank and reflected back by the liquid surface. In order to calculate the filling level, the propagation speed of the ultrasonic wave (i.e. its speed of sound) in the liquid, is needed. The speed of sound is determined by a second transmitter-receiver which is positioned at a side wall of the tank and which measures the time of flight through the liquid, across the horizontal diameter of the tank. Since the diameter is a known magnitude, the speed of sound of the ultrasonic pulse can directly be calculated.

In U.S. Pat. No. 6,925,870B2, another non-intrusive ultrasonic level sensor scheme is proposed in which the transmitter-receiver unit of an acoustic signal is located at a side wall of the vessel. Again, a first ultrasonic signal is emitted in horizontal direction and reflected back from the opposite side wall of the vessel. This signal is used for measuring the speed of sound, i.e. the travel speed of the ultrasonic beam, in the liquid. A second ultrasonic signal is emitted in an angular direction in such a way that it is reflected back by the intersection between the liquid surface and the opposite side wall of the vessel. From the previously determined speed of sound and from the time of flight of this second signal, the length of its inclined path is obtained. The height of the liquid surface relative to the location of the transducer is then calculated as the height of a right triangle having hypotenuse and leg corresponding to the lengths of the first and second ultrasonic travelling paths.

A prerequisite for the method of U.S. Pat. No. 6,925,870B2 to work is that the liquid surface, i.e. the level interface, and the vessel wall describe a rectangular corner. In other words, the method is only applicable to vessels with vertical walls. For non-vertically aligned walls, the ultrasonic signal would not be reflected back to the transmitter but to a different position, depending on the angle of the transmitted beam and the angle of the wall.

In general, the speed of sound in a liquid or in a gaseous medium depends on the chemical composition of the liquid or gas as well as on the temperature. Therefore, the propagation velocity may vary inside the medium. However, if the variation of the propagation velocity is low or if the requirements for the accuracy of the level measurements are low, the propagation velocity is assumed to be constant, as in both the JP2006322825A and the U.S. Pat. No. 6,925,870B2.

For some level measurement applications, where high accuracy is required, it is essential to determine the exact propagation velocity in the medium. This applies especially to acoustic level measurements, where a higher variation of the propagation speed of sound is to be expected. Accordingly, if there is a horizontal or vertical temperature gradient in the tank, the level measurement based on the obtained propagation speed value, as described in JP2006322825A and U.S. Pat. No. 6,925,870B2, may be inaccurate due to the significant temperature dependence of the propagation speed. For the example of ultrasound pulses propagating in water, the speed of sound varies by about 5% over a temperature gradient of 60° C., i.e. from 1,481 m/s at 20° C. to 1,555 m/s at 80° C.

In order to take temperature gradients into account, it is known from the art to determine the speed of sound in a medium by an empirical relation that uses the measured temperature of the medium as an input. Some more advanced systems provide a local propagation velocity measurement at the transmitter-receiver position.

However, in case the temperature gradients are extensive and/or local variations of the chemical composition of the medium occur the precision of an empirical estimation of the propagation velocity may not be sufficient. Also, it may not be feasible to measure the propagation velocity at several different locations due to mounting constraints, which especially applies for a non-intrusive level measurement system.

Therefore, it is an object of the present invention to provide an alternative system and an alternative method for measuring the speed of sound in a liquid or in a gaseous medium.

This object is achieved by a system and a method according to the independent claims.

According to the invention, at least one acoustic or electromagnetic transmitter, which is mounted on one side of the liquid surface, is arranged to transmit a first acoustic or electromagnetic signal in a first direction into the liquid or into the gaseous medium, wherein the first direction is at an acute or right first angle to a first reflective surface and along which first direction a gradient in the signal propagation speed is expected. The first reflective surface will then reflect the first signal so that it travels in a predetermined second direction and at the same first angle with respect to the first reflective surface.

The phrase "on one side" means hereby that the transmitter is placed in a horizontal plane which lies either above or below the liquid surface, and the transmitter may be mounted at the outside or at the inside of the vessel containing the liquid and the gaseous medium.

A first acoustic or electromagnetic receiver which is mounted on the same side of the liquid surface as the at least one transmitter is arranged to receive the reflected first signal. Accordingly, the receiver is placed in a horizontal plane which is above the liquid surface if the transmitter is above the liquid surface or below the liquid surface if the transmitter is below the liquid surface. The horizontal planes of the transmitter and of the receiver do not necessarily have to be the same, i.e. they can differ in their vertical positions. The receiver and the transmitter can be arranged in the same housing in form of a transducer.

The at least one transmitter is further arranged to transmit a second signal in a predetermined third direction which is at an acute or sharp second angle to the first direction, so that the second direction is non-perpendicular to the first or to a second reflective surface. The first or the second reflective surface, respectively, reflects the second signal so that it travels in a predetermined fourth direction and at an acute third angle with respect to the first or second reflective surface, respectively.

The first or, if applicable, a second acoustic or electromagnetic receiver which is also mounted on the same side of the liquid surface as the at least one transmitter is arranged to receive the reflected second signal.

At least one electronic control and data processing unit is adapted to
- control operation of the at least one transmitter and of the first and—if applicable—of the second receiver;
- determine a first time of flight of the first signal;
- determine a second time of flight of the second signal;
- determine the speed of sound under the assumption that both the first and the second signals travel at the same average speed. The determination is based on the first time of flight and a corresponding known first distance, the second time of flight and a corresponding known second distance, where the first and the second distance are different from each other and are either a distance between the at least one transmitter and the first or the second receiver, respectively, or a known geometric dimension of the vessel.

The term "time of flight" relates to the time which elapses between emission and reception of a signal.

The term "average speed" relates to the speed which is obtained by dividing a total distance travelled by a signal by the total time needed by the signal to cover the total distance.

The basic idea behind the invention is to use two independent measurements along two different propagation paths, wherein the two paths differ by their horizontal propagation component. The first signal is sent in an acute or right angle to and reflected from the first reflective surface and subsequently detected at a location that is different or the same as the location of the transmitter. A second signal is sent to the first or another reflective surface under an angle. The reflected part of the second signal is received by a second transducer or a second receiver.

If two receivers are used, the displacement between the transmitter and each of the receivers is known, and the sound of speed may be determined based on the time of flights of the first and second signals and on the respective distance between the transmitter and the receiver corresponding to the first or second signal, respectively.

If one and the same receiver is used for both signals, it is only able to receive the non-perpendicular, angular signal if it is mounted in a symmetric manner w.r.t. the geometry of the vessel. In this case, a corresponding geometric dimension of the vessel is used together with the two measured time of flights for determining the speed of sound. In particular, the geometric dimension may be the diameter of the vessel.

If either the first or the second signal is reflected from the liquid surface, it is possible to determine the level of the liquid surface, in addition to the signal propagation speed. In other words, in this case the level as well as the propagation velocity can be determined independently, based on the two measured propagation times.

The measurements can be performed from the inner top of the vessel, as it is generally done for intrusive level measurement devices, or from the bottom or the outside wall of the vessel, in case of a non-intrusive signal propagation speed measurement.

With the proposed system and method it becomes possible to calibrate the value of the signal propagation speed used in a level measurement system, thereby compensating for the variation of the propagation speed inside the vessel due to a vertical or a horizontal temperature gradient or temperature variation as well as due to a vertical or a horizontal layering of the chemical composition of the liquid or the gaseous medium.

The proposed system and method do not require any a-priori knowledge of, or any assumptions on, the medium and/or its temperature in the tank. Instead, the accuracy of the level measurement can be improved since the average speed of sound can be determined directly before or in connection with a level measurement, thereby ensuring that the present state of the medium as well as an intermediate change of medium or temperature are correctly taken into account.

Figure 1:
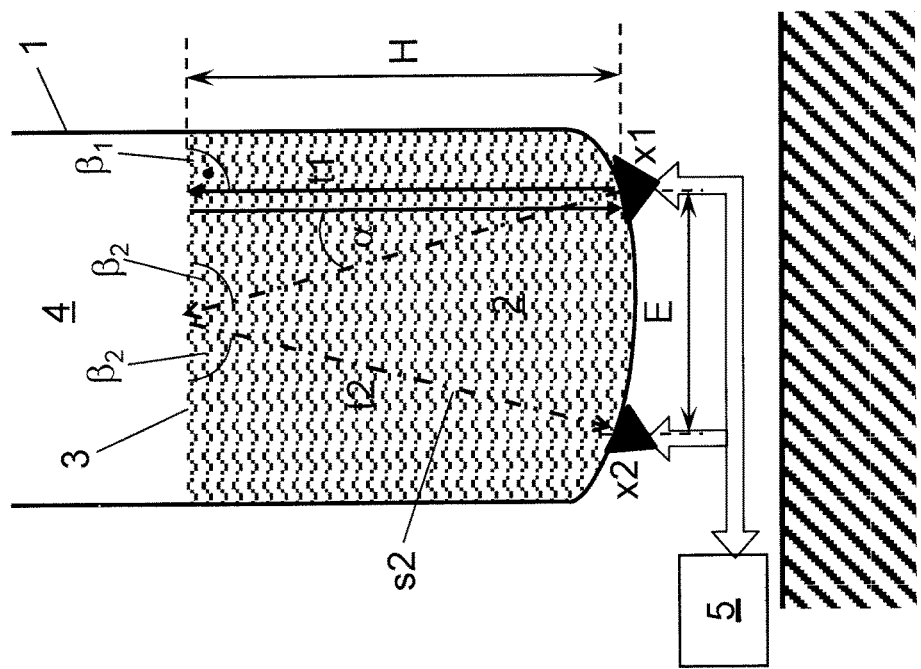
Figure 7:
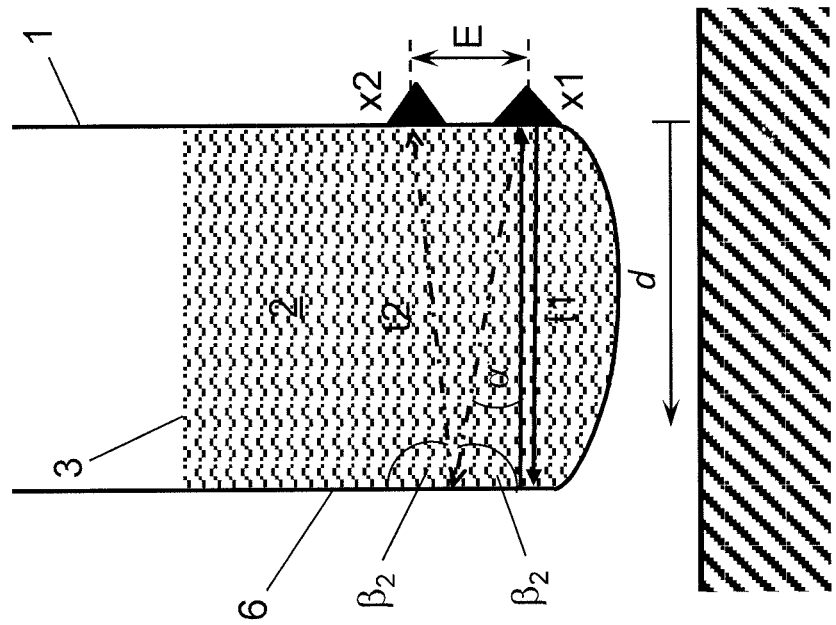
Figure 6:
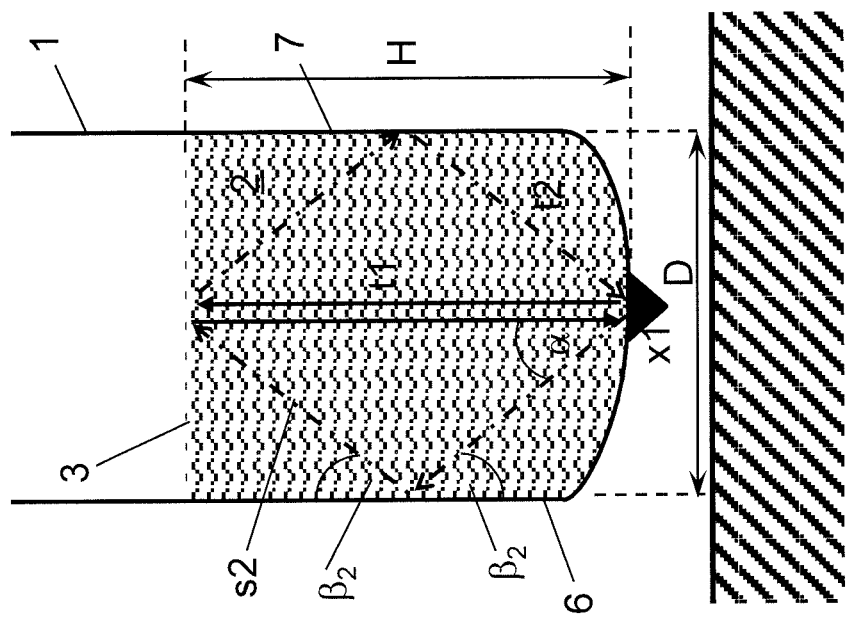
Figure 8:
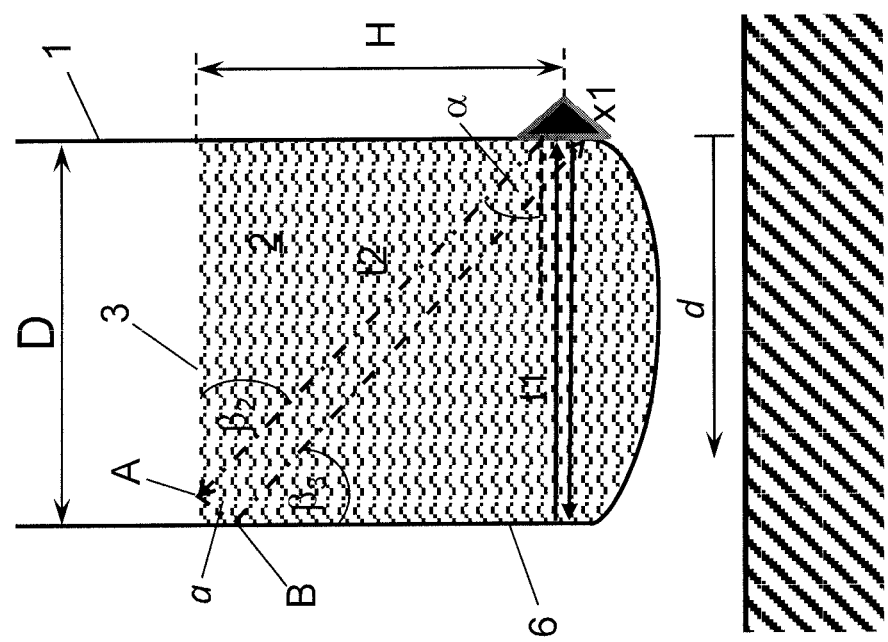

The invention and its embodiments will become even more apparent from the examples described below in connection with the appended drawings which illustrate:

FIG. 1 a first embodiment for measuring the signal propagation speed in a liquid;

FIG. 2 a second embodiment for measuring the signal propagation speed in a liquid;

FIG. 3 the first embodiment for measuring the signal propagation speed in a liquid, including measurement of the distance between transmitter and receiver;

FIG. 4 a second embodiment for measuring the signal propagation speed in a liquid, including measurement of the distances between respective transmitter and receiver;

FIG. 5 an embodiment for measuring the signal propagation speed in a gaseous medium above a liquid;

FIG. 6 a third embodiment for measuring the signal propagation speed in a liquid;

FIG. 7 a fourth embodiment for measuring the signal propagation speed in a liquid; and FIG. 8 a fifth embodiment for measuring the signal propagation speed in a liquid.

FIG. 1 shows a first embodiment for measuring the speed of sound in a liquid 2, where the liquid 2 is contained in a vessel 1 which has a solid wall. An acoustic transducer x1, into which a first acoustic transmitter and a first acoustic receiver are integrated, is mounted at the outside bottom of vessel 1, since it is expected or known that the speed of sound in liquid 2 varies vertically. Accordingly, transducer x1 is arranged to transmit a first acoustic signal in a first direction which is a vertical upward direction, wherein the vertical upward direction is perpendicular to the liquid surface 3, i.e. to the interface between the liquid 2 and a gas 4 that fills the space above the liquid. This is indicated by the first angle $\beta_1$, which is a right angle. The gas 4 may be for example air or a mixture of vaporized particles of liquid 2 and air.

The liquid surface 3 reflects back the first acoustic signal so that it travels in a second direction which is a vertical downward direction until it is received by the first receiver of transducer x1.

In addition, transducer x1 is further arranged to transmit a second signal in a third direction which is an angular upward direction. The third direction is at an acute second angle $\alpha$ with respect to the first direction and arrives at the liquid surface 3 at an acute third angle $\beta_2$.

The liquid surface 3 reflects the second signal so that it travels in a fourth direction which is an angular downward direction, maintaining the acute third angle $\beta_2$ to the liquid surface 3.

The first signal is indicated in all the figures by a dot-dashed line, while the second signal is indicated by a solid line.

The angular upward and downward directions of the second signal are chosen so that the reflected second signal is received by a second acoustic receiver x2. The second receiver x2 is mounted at the outside bottom of vessel 1 at a first distance E to the first transducer x1, and it may again be integrated in a transducer.

An electronic control and data processing unit 5 is provided which is adapted to control operation of transducer x1 and receiver x2 and to receive measurement signals from transducer x1 and receiver x2, where the measurement signals reflect the time periods elapsing between emission and reception of the first signal and of the second signal, called first time of flight t1 and second time of flight t2, respectively.

From these measurement signals, the electronic control and data processing unit 5 is adapted to obtain the first time of flight t1 of the first signal and the second time of flight t2 of the second signal and to determine the speed of sound in liquid 2 based on the assumption that both the first and the second signals travel at the same average speed and using the first time of flight t1, the second time of flight t2 and the known first distance E between the first and the second receivers.

Expressed in different words, FIG. 1 shows transducer x1 which sends a signal that propagates vertically, i.e. at a first angle which is a right angle to the liquid surface 3, and that is retro-reflected from the liquid surface 3 back to transducer x1. The corresponding pulse propagation time is t1 for the entire round trip. Transducer x1 sends a second signal towards the liquid surface 3 under a certain second angle, which is the acute angle $\alpha$ with respect to the vertical first direction, where the second signal is reflected from the liquid surface 3 to the receiver x2. The total propagation time of the second pulse from x1 to x2 is t2.

Based on geometrical considerations, which include the introduction of the magnitude s2 for half the length of the travel distance of the second signal, the signal propagation speed c may be calculated by the electronic control and data processing unit 5, independently of the liquid level H, by following equation:

$$c = \frac{E}{\sqrt{t_2^2 - t_1^2}} \quad (1)$$

The validity of equation (1) can be shown for the case that a vertical dependence of the propagation speed is present in liquid 2 (c=c(h)), i.e. the propagation speed depends on the height coordinate. This scenario is realistic if for example there is a vertical temperature gradient in the medium. In this case, t1 can be expressed as the integral of the propagation speed along the corresponding path:

$$t_1 = 2\int_0^H \frac{1}{c(h)} dh \quad (2)$$

Similarly, t2 can be expressed as $$t_2 = 2\int_0^S \frac{1}{c(h)} ds = 2\int_0^H \frac{\sqrt{H^2 + \left(\frac{D}{2}\right)^2}}{H} \frac{1}{c(h)} dh \quad (3)$$

with s being the path between x1 and the liquid surface 3 and by using the relation between ds and dh:

$$\frac{ds}{dh} = \frac{S}{H} = \frac{\sqrt{H^2 + \left(\frac{D}{2}\right)^2}}{H} \quad (4)$$

If now the ratio between t2 and t1 is considered, it is easy to prove that it is independent of c(h), that is the vertical dependence of the propagation speed—it depends in fact only on the vessel geometry:

$$\frac{t_2}{t_1} = \frac{\sqrt{H^2 + \left(\frac{D}{2}\right)^2}}{H} \quad (5)$$

From this it may be concluded that equation (1) delivers the average propagation speed that the pulse experiences during the propagation in the liquid 2.

The system of FIG. 1 for measuring the speed of sound in liquid 2 may additionally be used for determining the filling level H of vessel 1. In other words, since in the case of FIG. 1 both the first and second signals were reflected by the liquid surface, information is available to determine the level of the liquid in the vessel based on the determined speed of sound and based on the time of flights t1 and t2 of both signals.

The resulting equation for the filling level H is:

$$H = \frac{E}{2\sqrt{t_2^2/t_1^2 - 1}} \quad (6)$$

FIG. 2 shows a second embodiment for the measurement of the signal propagation speed in a liquid. The difference to FIG. 1 is that the propagation path of the first pulse is not perpendicular to the liquid surface 3. Accordingly, a first acoustic transmitter x3 is arranged to transmit a first signal in a first direction which is at an acute angle $\beta_1$ to a first reflective surface 3. The first signal is again shown by a straight line. Along this first direction, a variation or a gradient in the propagation speed of the acoustic signals is expected. The first reflective surface 3 reflects the first signal so that it travels in a predetermined second direction and at the same first angle $\beta_1$ with respect to the first reflective surface 3.

A first acoustic receiver x4 is arranged to receive the reflected first signal.

The first acoustic transmitter x3 is further arranged to transmit a second signal in a predetermined third direction which is at an acute second angle a to the first direction. The second signal is again shown by a dot-dashed line. The first reflective surface 3 reflects the second signal so that it travels in a predetermined fourth direction and at an acute third angle $\beta_2$ with respect to the first reflective surface 3.

A second acoustic receiver x5 is arranged to receive the reflected second signal.

An electronic control and data processing unit 5 is arranged to
  obtain a first time of flight t1 of the first signal;
  obtain a second time of flight (t2) of the second signal;
  determine the signal propagation speed under the assumption that both the first and the second signals travel at the same average speed. The determination is based on the first time of flight t1, a corresponding known first distance $E_1$, the second time of flight t2 and a corresponding known second distance $E_2$, where the first and second distance are different from each other ($E_1 \neq E_2$).

The first distance $E_1$ is the distance between the first transmitter x3 and the first receiver x4; and the second distance $E_2$ is the distance between the first transmitter x3 and the second receiver x5.

FIG. 3 shows the same embodiment as FIG. 1, with the difference that a Lamb wave 8 is used to measure the first distance E between first transducer x1 and second receiver x2.

Lamb waves or also called plate waves are mechanical waves generated in plates where the wave propagation is influenced by the reflection of the wave at the sides of the walls and the thus limited propagation space. They thus show similar properties as waves propagating in wave guides. Lamb waves are propagating in different modes with different properties, in particular different propagation velocities as well as different attenuations. Typically at low frequencies, a symmetric S0 and an anti-symmetric A0 mode can occur. Ideally, the waves are reflected totally at the sides of the plate and are thus kept inside the plate. From the time of flight of the Lamb wave 8 and provided that the speed of sound inside the wall of vessel 1 is known, the first distance E can be determined.

In FIG. 4, which corresponds to the embodiment of FIG. 2, a first Lamb wave 9 is used in the above described way to determine the first distance $E_1$ between first transmitter x3 and first receiver x4; and a second Lamb wave 10 is used analogously to determine the second distance $E_2$ between first transmitter x3 and second receiver x5.

FIG. 5 differs from FIG. 1 in that the speed of sound in the gaseous medium 4 above liquid 2 is determined and that an electromagnetic transducer, in particular a radar transducer x1 with integrated first transmitter and first receiver, and an electromagnetic receiver, in particular a radar receiver (x2) are used. The radar receiver is in the following called second receiver x2. The electronic control and data processing unit 5 is not depicted, as is also the case for the remaining FIGS. 4-6. While the solution of FIG. 1 is applicable to non-intrusive level measurement systems, the arrangement of FIG. 5 applies to intrusive level measurement techniques.

Apart from these differences, the same principles and conclusions apply as in FIG. 1.

FIG. 6 shows an alternative setup to FIG. 1, in the form of a third embodiment for measuring the speed of sound in a liquid. Again, the speed of sound in liquid 2 is assumed or expected to show a variation or gradient in vertical direction. The difference in the setup lies in that the two paths with the different horizontal components are generated by a single acoustic transducer x1 with an integrated first transmitter and first receiver. Here, the transducer x1 emits two beams or signals; one beam going straight upwards to the liquid surface 3, i.e. in a first direction and at a first angle which is a right angle w.r.t. the liquid surface 3. The liquid surface 3 may be regarded as a first reflective surface. The second beam is emitted under a predetermined acute second angle a with respect to the vertical first direction, and it arrives at the side wall 6 of the vessel under an acute third angle R2, wherein the side wall 6 represents a second reflective surface. The second beam is reflected at the side wall 6, then at the liquid surface 3 and again at the opposite side wall 7. Given that the diameter D of the tank or vessel 1 is known the propagation speed c and the level H can be individually determined based again on the same principles as described in connection with FIG. 1.

Similarly to the concept for a vertical dependence of the speed of sound, a horizontal dependence may be accounted for by a corresponding horizontal arrangement of a transducer x1 with an integrated first transmitter and first receiver, being placed at a vertical distance E from a second receiver x2, as shown in FIG. 7. Accordingly, if the propagation speed has a horizontal dependence in the tank or vessel 1, i.e. c=c(d), which may be the case for example due to a horizontal temperature gradient in the tank, the average propagation speed c can be determined by applying the measurement scheme of FIG. 7 and by following the same principles as described in connection with FIG. 1. The measurement scheme of FIG. 7 is limited in that the liquid surface 3 has to be above the second receiver x2.

A further variation of the propagation speed calibration scheme for a horizontal dependence of the speed of sound is depicted in FIG. 8. Here, only one transmitter and receiver is needed which are integrated in transducer x1. In FIG. 8, advantage is taken of an additional reflection of the second signal from the side wall 6 which results in an intermediate reflection path a between the reflection point A of the second signal at the liquid surface 3 and the reflection point B at the side wall 6. A similar configuration is used in U.S. Pat. No. 6,925,870B2, but there the second signal is used for level measurement purposes. The calibration scheme of FIG. 8 is again limited in that the liquid surface 3 has to be above transducer x1.

The first and second time of flights, t1 and t2, as well as the speed of sound c can be determined similarly as described in connection with FIG. 1. In the case of FIG. 6, however, c=c(d), i.e. the propagation velocity depends on the horizontal coordinate d instead of the vertical coordinate h. The overall horizontal dimension of vessel 1 is its diameter D. The propagation time or first time of flight t1 can be written as $$t_1 = 2 \int_0^D \frac{1}{c(d)} dd \quad (7)$$

Similarly, the second time of flight t2 can be expressed as $$t_2 = 2 \int_0^S \frac{1}{c(d)} ds \quad (8)$$

For the shortest second time of flight t2, the second signal must take the shortest possible round trip path, i.e. the pulse must be reflected from the corner between the side wall 6 of vessel 1 and the liquid surface 3. In other words, the length of intermediate path a equals to zero (a=0). To obtain the shortest second time of flight t2 is realistic, given the fact that the emitted beam of the second signal has a certain divergence. In this case, t2 can be written in the form $$t_2 = 2 \int_0^S \frac{1}{c(d)} ds = 2 \int_0^D \frac{\sqrt{H^2 + D^2}}{D} \frac{1}{c(d)} dd \quad (9)$$

Similarly to the description in connection with FIG. 1, it is possible to prove that the ratio between t2 and t1 is independent of c(d), that is the horizontal dependence of the propagation speed $$\frac{t_2}{t_1} = \frac{\sqrt{H^2 + D^2}}{D}. \quad (10)$$

Since the second signal is reflected by the liquid surface 3, the corresponding time of flight carries information about the liquid level H. Here, the liquid level H can be determined based on equation 9, resulting in equation (11). It is to be noted that equation (11) is again independent of the propagation velocity.

$$H = D\sqrt{t_2^2/t_1^2 - 1} \quad (11)$$

The above described concept for determining the signal propagation speed in connection with level measurement of a liquid is not limited in its applicability to liquids.

By using appropriate sending/receiving units it can be employed to determine the effective propagation speed of a pulse
   in the entire electromagnetic spectrum,
   for invasive and non-invasive techniques,
   for gas, liquid or solid media.

Potential applications may include e.g. the propagation speed measurement of radar pulses in the radio frequency (RF) domain, of light pulses in the optical domain, or of ultrasound pulses and/or waves, in an arbitrary medium (gas, liquid or solid), provided that the propagation speed in the corresponding medium is constant or has a one-dimensional gradient.

What is claimed is:

1. System for measuring a signal propagation speed in a liquid which is contained in a vessel, or in a gaseous medium which is contained in the same vessel above the surface of the liquid, the system comprising
   at least one acoustic or electromagnetic transmitter mounted on one side of the liquid surface for transmitting a signal into the liquid or into the gaseous medium,
   at least one acoustic or electromagnetic receiver mounted on the same side of the liquid surface as the at least one transmitter for receiving a reflection of the signal,
   at least one electronic control and data processing unit for controlling operation of the at least one transmitter and of the at least one receiver and for determining the signal propagation speed from a time of flight of the signal,
   wherein the at least one transmitter is arranged to transmit a first signal in a first direction which is at an acute or right first angle to a first reflective surface, along which first direction a variation or a gradient in the signal propagation speed is expected, wherein the first reflective surface reflects the first signal so that it travels in a predetermined second direction and at the same first angle with respect to the first reflective surface;
   a first acoustic or electromagnetic receiver is arranged to receive the reflected first signal;
   the at least one transmitter is further arranged to transmit a second signal in a predetermined third direction which is at an acute second angle to the first direction, where the first or a second reflective surface reflects the second signal so that it travels in a predetermined fourth direction and at an acute third angle with respect to the first or second reflective surface, respectively;
   the first or a second acoustic or electromagnetic receiver is arranged to receive the reflected second signal;
   the at least one electronic control and data processing unit is arranged to
      obtain a first time of flight of the first signal;
      a obtain a second time of flight of the second signal;
      determine the signal propagation speed under the assumption that both the first and the second signal travel at the same average speed and based on the first time of flight, a corresponding known first distance, the second time of flight and a corresponding known second distance, where the first and second distance are different from each other and are either a distance between the at least one transmitter and the first or the second receiver, respectively, or a known geometric dimension of the vessel.

2. System according to claim 1, wherein the known geometric dimension is the diameter of the vessel.

3. System according to claim 1, wherein the first reflective surface is the liquid surface.

4. System according to claim 3, wherein the second reflective surface is the side wall of the vessel.

5. System according to claim 1, wherein the first reflective surface is a side wall of the vessel which lies opposite to the side where the at least one transmitter is mounted at.

6. System according to claim 5, wherein the second reflective surface is the liquid surface.

7. System according to claim 1, wherein the at least one transmitter and the first receiver are integrated in the same device.

8. Method for measuring a signal propagation speed in a liquid which is contained in a vessel, or in a gaseous medium which is contained in the same vessel above the surface of the liquid, the method comprising the steps:
   transmitting a signal into the liquid or into the gaseous medium by at least one acoustic or electromagnetic transmitter mounted on one side of the liquid surface,
   receiving a reflection of the signal by at least one acoustic or electromagnetic receiver mounted on the same side of the liquid surface as the at least one transmitter,
   at least one electronic control and data processing unit for controlling operation of the at least one transmitter and of the at least one receiver, for determining a time of flight of the signal and for determining the signal propagation speed from the time of flight, wherein transmitting by the at least one transmitter a first signal in a first direction which is at an acute or right first angle to a first reflective surface, along which first direction a variation or a gradient in the signal propagation speed is expected, wherein the first reflective surface reflects the first signal so that it travels in a predetermined second direction and at the same first angle to the first reflective surface;

receiving the reflected first signal by a first acoustic or electromagnetic receiver;

transmitting by the at least one transmitter a second signal in a predetermined third direction which is at an acute second angle to the first direction, where the first or a second reflective surface reflects the second signal so that it travels in a predetermined fourth direction and at an acute third angle with respect to the first or second reflective surface, respectively;

receiving the reflected second signal by the first or a second acoustic or electromagnetic receiver;

via the at least one electronic control and data processing unit:
  obtaining a first time of flight of the first signal;
  obtaining a second time of flight of the second signal;
  determining the signal propagation speed under the assumption that both the first and the second signal travel at the same average speed and based on the first time of flight, a corresponding known first distance, the second time of flight and a corresponding known second distance, where the first and second distance are different from each other and are either a distance between the at least one transmitter and the first or second receiver, respectively, or a known geometric dimension of the vessel.

9. Method according to claim 8, wherein in case that the first or second reflective surface is the liquid surface, the level of the liquid in the vessel is determined based on the determined signal propagation speed and based on the time of flights of the first and second signals.

10. System according to claim 2, wherein the first reflective surface is the liquid surface.

11. System according to claim 10, wherein the second reflective surface is the side wall of the vessel.

12. System according to claim 2, wherein the first reflective surface is a side wall of the vessel which lies opposite to the side where the at least one transmitter is mounted at.

13. System according to claim 12, wherein the second reflective surface is the liquid surface.

14. System according to 2, wherein the at least one transmitter and the first receiver are integrated in the same device.

15. System according to 3, wherein the at least one transmitter and the first receiver are integrated in the same device.

16. System according to 4, wherein the at least one transmitter and the first receiver are integrated in the same device.

17. System according to 5, wherein the at least one transmitter and the first receiver are integrated in the same device.

18. System according to 6, wherein the at least one transmitter and the first receiver are integrated in the same device.

19. System according to 12, wherein the at least one transmitter and the first receiver are integrated in the same device.

20. System according to 11, wherein the at least one transmitter and the first receiver are integrated in the same device.

* * * * *